United States Patent [19]

Jung et al.

[11] Patent Number: 5,726,336

[45] Date of Patent: Mar. 10, 1998

[54] POLYALKYLATED BENZENES CONTAINING CHLOROSILYL GROUPS AND THEIR PREPARATION METHODS

[75] Inventors: Il Nam Jung; Joon Soo Han; Eun Jeong Cho, all of Seoul; Bok Ryul Yoo, Kyung-Gi Do, all of Rep. of Korea

[73] Assignee: Korea Institute of Science and Technology, Seoul, Rep. of Korea

[21] Appl. No.: 753,749

[22] Filed: Nov. 29, 1996

[30] Foreign Application Priority Data

Dec. 9, 1995 [KR] Rep. of Korea ............... 48114/1995

[51] Int. Cl.$^6$ ...................................... C07F 7/08
[52] U.S. Cl. ............................. 556/431; 556/432
[58] Field of Search ...................... 556/432, 431

[56] References Cited

U.S. PATENT DOCUMENTS

| | | | |
|---|---|---|---|
| 2,626,269 | 1/1953 | Barry | 556/432 |
| 3,137,720 | 6/1964 | Cooper | 556/432 |
| 3,686,252 | 8/1972 | Bazouin et al. | 556/432 |
| 5,113,003 | 5/1992 | Woods et al. | 556/432 |

*Primary Examiner*—Paul F. Shaver
*Attorney, Agent, or Firm*—Oblon, Spivak, McClelland, Maier & Neustadt, P.C.

[57] ABSTRACT

Polyalkylated benzenes containing chlorosilyl groups represented by formula III

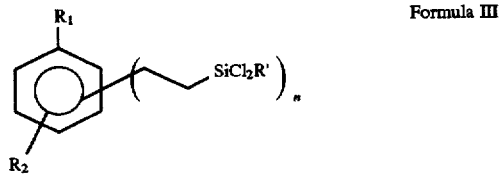

wherein $R_1$ represents hydrogen or alkyl; $R_2$ represents hydrogen or alkyl; R' represents methyl or chloro; and n=3–6.

20 Claims, No Drawings

POLYALKYLATED BENZENES CONTAINING CHLOROSILYL GROUPS AND THEIR PREPARATION METHODS

BACKGROUND OF THE INVENTION

1. Field of the Invention

The present invention relates to polyalkylated benzenes containing chlorosilyl groups and to a process for the preparation of the compounds by reacting a benzene compound with a vinylchlorosilane.

2. Description of the Background

In 1877, Friedel and Crafts first reported that when benzene is reacted with alkyl chloride in the presence of aluminum chloride catalyst, benzene is substituted with the alkyl group of the alkyl chloride. Under the same reaction conditions, acyl chloride is also known to react with benzene to give acylbenzene. The Friedel-Crafts alkylation and acylation reactions have been widely used as synthetic procedures for alkyl or acyl group substituted aromatic compounds in the laboratory and on the commercial scale as well. (Friedel, C.; Crafts, J. M., Bull. Soc. Chim. France, 27(2), 530, 1877).

In 1879, Balson reported that aromatic compounds react with olefins in the presence of Lewis acids such as aluminum chloride, the reaction being an addition reaction of olefin to the aromatic compounds. (Balson, M., Bull. Soc. Chim. France, 1879, 2, 31, 539) This Friedel/Crafts type alkylation has been widely used for the preparation of ethylbenzene and isopropylbenzene in the petrochemical industry. (Yoneda, N., Sekiyu Gakkai Shi, 1972, 15(11), 894).

Friedel-Crafts also reported obtaining a mixture of toluene, xylenes, durene, and penta- and hexamethylbenzene from a reaction of benzene with methyl chloride in the presence of aluminum chloride. (Friedel, C.; Crafts, J. M., Compt., rend. 1877, 84, 1392). Anschutz and Immendorff reported that methylated benzenes from mono- to hexamethylated benzene were obtained from the reaction of methyl chloride with benzene and the distribution of each component varied depending upon the reaction conditions such as mixing ratios of the reactants and reaction time. They also obtained similar results from the reaction of ethyl chloride with benzene. (Anschutz, R., Immendorff, H. Ber. 1885, 18, 657).

In 1957, Chernyshev and Dolgaya reported first that aromatic compounds can be alkylated with chloroethyl group containing chlorosilanes. They obtained trichlorosilylethyl substituted aromatic compounds from the Friedel-Crafts alkylation with chloroethyl trichlorosilane in good yields from 30 to 83%. (Chernyshev, E. A.; Dolgaya, M. E., Zhur. Obshchei Khim. 1957, 27, 48–51) In 1953, Wagner et al. reported that vinylchlorosilanes can be added to aromatic compounds in the presence of aluminum chloride catalyst. They obtained β-phenylethyltrichlorosilane as the major product and bis(trichlorosilylethyl)benzene as a minor product from the reaction of vinyltrichlorosilane with benzene. (Wagner, G. H.; Bailey, D. L.; Pines, A. N.; Dunhum, M. L. and McIntire, D. B., Industrial and Engineering Chemistry 1953, 45, 367). In 1961, Andrianov et al. reported that bis(chlorosilylethyl)benzene can be prepared in yields from 30 to 50% by reacting benzene with sufficient vinylchlorosilane. (Andrianov, K. B.; Zhdanov, A. A. and Odinets, V. A., Zh. Obshch. Khim., 1961, 31, 4033–8; Andrianov, K. B.; Zhdanov, A. A. and Odinets, V. A., Zh. Obshch. Khim., 1962, 38(3), 627–31).

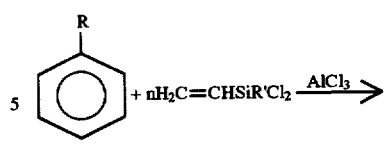

$R = H, Cl, Me; R' = Me, Et, Cl, n = 1, 2$

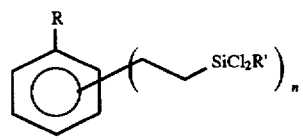

In 1966, Nametkin et al. reported that substituted benzenes can be alkylated with allylchlorosilanes such as allyldichlorosilane and allyltrichlorosilane to give (2-arylpropyl)chlorosilanes. The yields ranged from 34% to 66%, depending upon the benzene ring substituents, but information concerning product isomer distribution was not reported. (Nametkin, N. S.; Vdovin, V. M.; Finkelshtein, E. S.; Oppengeium, V. D. and Chekalina, N. A., Izv. Akad. Nauk SSSR, Ser. Khim., 1966, (11) 1998–2004).

The present inventors reported the preparation of (2-arylpropyl)dichlorosilanes by the Friedel-Crafts alkylation of various substituted aromatic compounds with allyldichlorosilane in the presence of Lewis acid catalysts in good yields ranging from 60% to 80%. (Lee, B. W.; Yoo, B. R.; Kim, S. I.; Jung, I. N., Organometallics 1994, 13, 1312). In this reaction, bis-alkylated aromatic compounds were obtained by controlling the reaction conditions such as the mole ratio of the reactants. However, the yield of polyalkylated compounds was very low probably because of the steric hindrance of silyl group containing isopropyl groups.

SUMMARY OF THE INVENTION

Accordingly, one object of the present invention is to provide a method of preparing polyalkylated benzene compounds containing chlorosilyl groups.

Briefly, this object and other objects of the present invention as hereinafter will become more readily apparent can be attained by polyalkylated benzenes containing chlorosilyl groups of formula III:

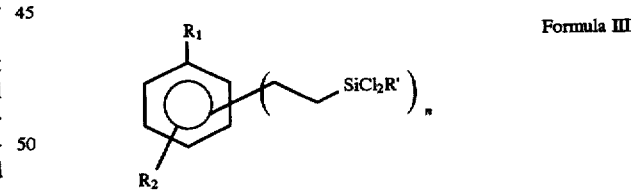

Formula III wherein $R_1$ is hydrogen or alkyl, $R_2$ is hydrogen or alkyl, R' is methyl or chloro and n is an integer of 3 to 6.

The polyalkylated benzene containing chlorosilyl groups is prepared by reacting a vinylchlorosilane of formula II with a benzene compound of formula I in the presence of a Lewis acid catalyst.

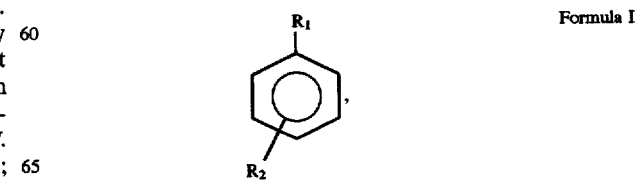

Formula I

-continued

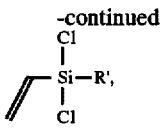

Formula II wherein $R_1$, $R_2$ and R' are as defined above.

DETAILED DESCRIPTION OF THE PREFERRED EMBODIMENTS

The alkylation reactions of the present invention can be conducted in standard laboratory glassware or commercial equipment, under inert atmosphere, with units for external cooling and heating, stirring, and for incremental addition of the starting aromatic compounds or vinylchlorosilanes. The reaction can be carried out in most of the nonaromatic hydrocarbon solvents, but it also proceeds under neat conditions. Any hydrocarbon solvent which is inert to the Freidel-Crafts reaction conditions may be used in the present invention. Suitable solvents include carbon disulfide, petroleum ether, ethylene chloride, methylene chloride, and carbon tetrachloride. Alternatively, the reaction may be run with an excess of the benzene compound as solvent.

Suitable Lewis acid catalysts include any Lewis acid catalyst which will function as a Freidel-Crafts catalyst. Freidel-Crafts catalysts are electron acceptors and are well known in the art. Suitable catalysts are described, for example, in Encyclopedia of Chemical Technology, 1980, vol. 11, pp. 292–297. Suitable catalysts include, but are not limited to $AlCl_3$, $AlBr_3$, $AlI_3$, $GaCl_3$, $GaCl_2$, $GaBr_3$, $GaI_3$, $ZrCl_4$, $HfCl_4$, $HfBr_4$, $HfI_4$, $SbF_5$, $NbF_5$, $NbCl_5$, $TaF_5$, $TaCl_5$, $TaBr_5$, $MoF_6$ and $MoCl_5$. A preferred catalyst is aluminum chloride ($AlCl_3$). The catalyst is used in an amount sufficient to catalyze the reaction; generally, in an amount of about 0.001–0.1 moles of catalyst per mole of the vinylchlorosilane.

As used herein, the term "alkyl" means an alkyl group which enables the vinylchlorosilane and the benzene compound to undergo the desired Freidel-Crafts reaction. One having ordinary skill in this art can easily determine the degree of branching and number of carbon atoms in suitable alkyl groups with a few preliminary experiments in which the product mixture is analyzed to determine the presence of the polyalkylated benzene. The product mixture may be analyzed using any suitable well-known method, for example, high pressure liquid chromatography, thin layer chromatography, etc. Preferably, $R_1$ is hydrogen or a linear or branched alkyl group having 1–10 carbon atoms, more preferably 1–4 carbon atoms. $R_2$ is preferably hydrogen or a linear or branched alkyl group having 1–4 carbon atoms, preferably 1–2 carbon atoms, more preferably methyl.

In a typical preparation, benzene compounds represented by formula I and catalyst are placed in the reactor under inert atmosphere. A vinyl-chlorosilane represented by formula II is then slowly added to the solution with stirring. The reaction may be exothermic, but it is desirable to maintain the reaction temperature below 80° C. by controlling the rate of addition of reactant or by continuously carrying out external cooling. Depending upon the targeted alkylation compound, vinylchlorosilanes represented by formula II may be used in a 0.01 to 20 fold amount, preferably a 4 to 10 fold amount, relative to the benzene derivative represented by formula I in terms of molar quantities. After completion of addition, heating and stirring may be carried out for certain period of time, generally about 10 minutes to about 10 hours, to complete the alkylation and then the solid products may be filtered and the liquid products fractionally distilled at atmosphere or under vacuum.

The polyalkylated aromatic compounds containing silicon-chlorine bonds of the invention can be functionalized by reaction with organolithium compounds and can be polymerized by hydrolysis to produce silicon polymers in a process which is analogous to the well-known chlorosilane hydrolysis of chlorosilane monomers to produce silicone polymers. See, for example, the discussion of silicone polymers and methods of making these polymers described in Encyclopedia of Chemical Technology, 1982, vol. 20, pps. 922–962 and the references cited therein. The silicone polymers prepared from the monomers of the present invention are suitable for use as emulsions, greases, adhesives, sealants, coatings, etc. in the automotive and engineering fields.

EXAMPLES

Having generally described this invention, a further understanding can be obtained by reference to certain specific examples which are provided herein for purposes of illustration only and are not intended to be limiting unless otherwise specified.

Example 1

Reaction of Benzene With Vinyldichloromethylsilane

To a 100 ml, three necked, round bottomed flask equipped with a mechanical stirrer, a dropping funnel, and a reflux condenser, 0.10 g (0.75 mmol) of aluminum chloride and 0.87 g (11.00 mmol) of benzene were placed under a dry nitrogen atmosphere. To the solution, 10.87 g (77.0 mmol) of vinyldichloromethylsilane was added dropwise while the flask was immersed in a water bath. The temperature of the water bath was increased from 25° C. to 50° C. because of the exothermic nature of the alkylation reaction. After completion of addition, the solution was stirred vigorously for another two hours. The water temperature dropped down to room temperature again and some solid precipitated out of solution. 20 ml of dried hexane and 10.3 g (0.0051 mol) of NaCl were added to the solution and the solution was stirred at 80° C. for 2 hours to deactivate aluminum chloride catalyst. The solid mixture was filtered and THF was added to dissolve the organic product. After filtering off NaCl, a recrystallization from THF gave 4.41 g (yield; 39.3%, mp; 165°–75° C.) of hexakis(methyldichlorosilylethyl)benzene.

On the other hand, vacuum distillation of the filtrate gave 1.16 g (yield; 10.3%), 1.52 g (yield; 13.5%), 1.17 g (yield; 10.4%, bp; 165°–70° C./0.6 mm), 0.58 g (yield; 5.17%, bp; 200°–4° C./0.6 mm), 0.96 g (8.53%, bp; 255°–9° C./0.6 mm) of mono-, bis-, tris-, tetrakis-, pentakis (methyldichlorosilylethyl)benzenes respectively. NMR data of the polyalkylated products prepared as above are listed in Table 1.

TABLE 1

$^1$H NMR data of poly(methyldichlorosilylethyl)benzenes

| No. of subst. | NMR data (ppm) | | | |
|---|---|---|---|---|
| (n) | Si—$CH_3$ | Si—$CH_2$ | Aryl-$CH_2$ | Aryl-H |
| 3 | 0.82 (s) | 1.42–1.52 (m) | 2.80–2.90 (m) | 7.08–7.22 (m) |
| 4 | 0.83 (s) | 1.42–1.52 (m) | 2.80–2.90 (m) | 7.03 (s) |

TABLE 1-continued $^1$H NMR data of poly(methyldichlorosilylethyl)benzenes

| No. of subst. | NMR data (ppm) | | | |
|---|---|---|---|---|
| (n) | Si—CH$_3$ | Si—CH$_2$ | Aryl-CH$_2$ | Aryl-H |
| 5 | 0.84 (s) | 1.42–1.52 (m) | 2.80–2.90 (m) | 6.97 (s) |
| 6 | 0.87 (s) | 1.29–1.36 (m) | 2.71–2.77 (m) | * |

| No. of Subst. | NMR data (ppm) | | | | | |
|---|---|---|---|---|---|---|
| (n) | Si—CH$_3$ | Et(CH$_3$) | Si—CH$_2$ | Et(CH$_2$) | Aryl—CH$_2$ | Aryl—H |
| 3 | 0.59–0.75(m) | 1.19–1.21(m) | 1.42–1.49(m) | 2.58–2.60(m) | 2.71–2.77(m) | 7.01–7.09(m) |
| 4 | 0.81–0.83(m) | 1.19–1.21(m) | 1.42–1.49(m) | 2.58–2.60(m) | 2.71–2.77(m) | 6.95(s) |
| 5 | 0.87(m) | 1.20(t) | 1.29–1.36(m) | 2.59(q) | 2.71–2.77(m) | — |

Example 2

Reaction of Toluene With Vinyldichloromethylsilane

In the same apparatus and by the same procedure of EXAMPLE 1, 0.88 g (9.35 mmol) of toluene, 9.78 g (69.35 mmol) of vinyldichloromethylsilane and 0.12 g (0.90 mmol) of aluminum chloride were reacted for 1 hour under a dry nitrogen atmosphere. Recrystallization of solid product from THF gave 4.55 g (yield; 61.16%, mp; 254°–6° C.) of white crystalline pentakis(methyldichlorosilylethyl)toluene. Distillation of the filtrate gave 0.11 g (yield; 1.48%), 0.14 g (yield; 1.88%), 0.48 g (yield; 6.18%, bp; 179°–82° C./0.6 mm), 0.86 g (yield; 11.56%, bp; 214°–8° C./0.6 mm) of mono-, bis-, tris-, and tetrakis(methyldichlorosilylethyl) toluenes, respectively. Isomeric mixtures were also obtained. NMR data of the polyalkylated products prepared as above are listed in Table 2.

Table 2. $^1$H NMR data of poly(methyldichlorosilylethyl) toluenes

| No. of Subst | NMR data (ppm) | | | | |
|---|---|---|---|---|---|
| (n) | Si—CH$_3$ | Si—CH$_2$ | Aryl—CH$_3$ | Aryl—CH$_2$ | Aryl—H |
| 3 | 0.82–0.99(m) | 1.22–1.45(m) | 2.30–2.38(m) | 2.65–2.91(m) | 6.93–7.14(m) |
| 4 | 0.91(s) | 1.22–1.35(m) | 2.32(s) | 2.85–2.91(m) | 6.93(m) |
| 5 | 0.86(s) | 1.27–1.34(m) | 2.27(s) | 2.73–2.83(m) | * |

Example 3

Reaction of Ethylbenzene With Vinyldichloromethylsilane

In the same apparatus and by the same procedure described in EXAMPLE 1, 0.87 g (8.20 mmol) of ethylbenzene, 5.76 g (41.00 mmol) of vinyldichloromethylsilane and 0.01 g (0.082 mmol) of aluminum chloride were reacted for 3 hours under a dry nitrogen atmosphere. Recrystallization of solid product from THF gave 1.66 g (yield; 25.0%, mp; 185°–8° C.) of white crystalline pentakis(methyldichlorosilylethyl)ethylbenzene. Distillation of the filtrate gave 0.069 g (yield; 1.04%), 0.29 g (yield; 4.38%, bp; 165°–9° C./0.6 mm), 0.586 g (yield; 8.73%, bp; 211°–6° C./0.6 mm), 0.12 g (yield; 1.81%), 0.71 g (yield; 10.7%), 0.75 g (yield; 11.3%), 0.32 g (yield; 4.83%), 0.43 g (yield; 6.55%) and 0.52 g (yield; 7.86%) of bis-, tris-, tetrakis(methyldichlorosilylethyl)ethylbenzenes, bis-, tris-, tetrakis(methyldichlorosilylethyl)diethylbenzenes, tris-, tetrakis- and pentakis(methyldichlorosilylethyl)benzenes, respectively. Isomeric mixtures were also obtained. NMR data of the polyalkylated products prepared as above are listed in Table 3.

Example 4

Reaction of n-propylbenzene With Vinyldichloromethylsilane

In the same apparatus and by the same procedure as described in EXAMPLE 1, n-propylbenzene 0.86 g (7.17 mmol), vinyldichloromethylsilane 5.06 g (35.90 mmol) and aluminum chloride 0.047 g (0.35 mmol) were reacted for 1 hour under a dry nitrogen atmosphere. Recrystallization of solid product from THF gave 1.59 g (yield; 26.8%, mp; 201°–6° C.) of white crystalline pentakis(methyldichlorosilylethyl)-n-propylbenzene. Distillation of the filtrate gave 0.40 g (yield; 6.57%), 0.60 g (yield; 10.1%), 0.66 g (yield; 11.1%; bp: 182°–8° C./0.6 mm), 0.78 g (yield: 13.1%, bp; 210°–5° C./0.6 mm), 0.48 g (yield: 8.15%), 0.062 g (yield: 1.05%), and 0.094 g (yield: 1.59%) of mono-, bis-, tris-, tetrakis(methyldichlorosilylethyl)-n-propylbenzenes, tetrakis(methyldichlorosilylethyl)dipropylbenzenes, mono- and bis(methyldichlorosilylethyl)benzenes, respectively. Isomeric mixtures were also obtained. NMR data of the polyalkylated products prepared as above are listed in Table 4.

Table 4. $^1$H NMR data of poly(methyldichlorosilylethyl)-n-propylbenzenes

| No. of Subst. | NMR data (ppm) | | | | | | |
|---|---|---|---|---|---|---|---|
| (n) | Si—CH$_3$ | Pr(CH$_3$) | Si—CH$_2$ | Pr(CH$_2$) | Pr(CH$_2$) | Aryl—CH$_2$ | Aryl—H |
| 3 | 0.59–0.76(m) | 1.00–1.02(m) | 1.43–1.50(m) | 1.49–1.54(m) | 2.50–2.52(m) | 2.71–2.79(m) | 7.01–7.09(m) |
| 4 | 0.83, 0.84(s) | 1.00–1.02(m) | 1.43–1.50(m) | 1.49–1.54(m) | 2.50–2.52(m) | 2.71–2.79(m) | 6.95(s) |
| 5 | 0.87(s) | 1.01(t) | 1.30–1.37(m) | 1.49–1.54(m) | 2.51(t) | 2.71–2.79(m) | * |

Example 5

Reaction of n-butylbenzene With Vinyldichloromethylsilane

In the same apparatus and by the same procedure as described in EXAMPLE 1, n-butylbenzene 0.86 g (6.40 mmol), vinyldichloromethylsilane 4.52 g (32.00 mmol) and aluminum chloride 0.047 g (0.35 mmol) were reacted for 1 hour under a dry nitrogen atmosphere. Recrystallization of solid product from THF gave 1.35 g (yield: 26.8%, mp; 218°–25° C.) of white crystalline pentakis (methyldichlorosilylethyl)-n-butylbenzene. Distillation of the filtrate gave 0.34 g (yield: 6.75%), 0.51 g (yield: 10.1%), 0.56 g (yield: 11.1%, bp: 182°–8° C./0.6 mm), 0.66 g (yield: 13.1%, bp: 210°–5° C./0.6 mm), 0.41 g (yield: 8.15%), 0.053 g (yield: 1.05%) and 0.08 g (yield: 1.59%) of mono-, bis-, tris-, tetrakis(methyldichlorosilylethyl)-n-butylbenzenes, tetrakis(methyldichlorosilylethyl) dibutylbenzene, mono- and bis(methyldichlorosilylethyl) benzenes respectively. Isomeric mixtures were also obtained. NMR data of the polyalkylated products prepared as above are listed in Table 5.

num chloride 0.096 g (0.72 mmol) were reacted for 2 hours under a dry nitrogen atmosphere. Recrystallization of solid product from THF gave 1.50 g (yield: 29.07%) of white crystalline tetrakis(methyldichlorosilylethyl)-p-xylene. Distillation of the filtrate gave 0.08 g (yield: 1.16%), 0.24 g (yield: 4.65%), 0.48 g (yield; 9.30%, bp: 183°–8° C./0.6 mm), 2.37 g (yield: 45.93%, bp: 230°–2° C./0.6 mm) and 0.05 g (yield: 0.97%) of mono-, bis-, tris-, tetrakis (methyldichlorosilylethyl)-o-xylenes and tetrakis (methyldichlorosilylethyl)toluene, respectively. Isomeric mixtures were also obtained. NMR data of the polyalkylated products prepared as above are listed in Table 6.

TABLE 5

$^1$H NMR data of poly(methyldichlorosilylethyl)-n-butylbenzenes

| No. of Subst. | NMR data (ppm) | | | | | | |
|---|---|---|---|---|---|---|---|
| (n) | Si—CH$_3$ | Bu(CH$_3$) | Si—CH$_2$ | Bu(CH$_2$CH$_2$) | Bu(CH$_2$) | Aryl—CH$_2$ | Aryl—H |
| 3 | 0.59–0.78(m) | 1.00–1.02(m) | 1.45–1.51(m) | 1.49–1.54(m) | 2.51–2.53(m) | 2.71–2.79(m) | 7.01–7.09(m) |
| 4 | 0.83–0.84(s) | 1.00–1.02(m) | 1.45–1.51(m) | 1.49–1.54(m) | 2.51–2.53(m) | 2.71–2.79(m) | 6.95(s) |
| 5 | 0.87(s) | 1.01(t) | 1.32–1.38(m) | 1.49–1.54(m) | 2.52(t) | 2.71–2.79(m) | * |

Example 6

Reaction of o-xylene With Vinyldichloromethylsilane

In the same apparatus and by the same procedure as described in EXAMPLE 1, o-xylene 0.87 g (8.21 mmol), vinyldichloromethylsilane 6.95 g (49.34 mmol) and alumi-

TABLE 6

$^1$H NMR data of poly(methyldichlorosilylethyl)-o-xylenes

| No. of Subst. | NMR data (ppm) | | | | |
|---|---|---|---|---|---|
| (n) | Si—CH$_3$ | Si—CH$_2$ | Aryl—CH$_3$ | Aryl—CH$_2$ | Aryl—H |
| 3 | 0.82–1.00(m) | 1.12–1.45(m) | 2.19–2.33(m) | 2.85–2.97(m) | 6.92–7.12(m) |
| 4 | 0.91(s) | 1.12–1.45(m) | 2.28(s) | 2.65–2.97(m) | * |

Example 7

Reaction of m-xylene With Vinyldichloromethylsilane

In the same apparatus and by the same procedure as EXAMPLE 1, m-xylene 0.87 g (8.20 mmol), vinyldichloromethylsilane 4.60 g (22.00 mmol) and aluminum chloride 0.14 g (0.82 mmol) were reacted for 2 hours under a dry nitrogen atmosphere. Recrystallization of solid product from THF gave 1.34 g (yield: 24.5%) of white crystalline tetrakis (methyldichlorosilylethyl)-P-xylene. Distillation of the filtrate gave 0.82 g (yield: 15.0%), 0.25 g (yield: 4.58%), 2.14 g (yield: 39.1%, bp; 182°–8° C./0.6 mm) and 0.25 g (yield: 4.56%, bp: 230°–5° C./0.6 mm) of mono-, bis-, tris- and tetrakis(methyldichlorosilylethyl)-m-xylenes, respectively. Isomeric mixtures were also obtained. NMR data of the polyalkylated products prepared as above are listed in Table 7.

TABLE 7

1H NMR data of poly(methyldichlorosilyl-ethyl)-m-xylenes

| No. of Subst. | NMR data (ppm) | | | | |
|---|---|---|---|---|---|
| (n) | Si—CH$_3$ | Si—CH$_2$ | Aryl—CH$_3$ | Aryl—CH$_2$ | Aryl—H |
| 3 | 0.80, 0.84(s) | 1.36–1.49(m) | 2.23–2.28(m) | 2.80–2.85(m) | 6.90(s) |
| 4 | 0.88(s) | 1.28–1.34(m) | 2.29(s) | 2.80–2.85(m) | * |

Example 8

Reaction of p-xylene With Vinyldichloromethylsilane

In the same apparatus and by the same procedure as described in EXAMPLE 1, p-xylene 0.87 g (8.20 mmol), vinyldichloromethylsilane 4.60 g (22.00 mol) and aluminum chloride 0.22 g (1.65 mmol) were reacted for 1 hour under a dry nitrogen atmosphere. Recrystallization of solid product from THF gave 3.48 g (yield: 63.6%, mp: 193°–8° C.) of white crystalline tetrakis(methyldichlorosilylethyl)-p-xylene. Distillation of the filtrate gave 0.82 g (yield: 15.0%), 0.25 g (yield: 4.58%) and 0.71 g (yield: 12.98, bp: 182°–8° C./0.6 mm) of mono-, bis- and tris(methyldichlorosilylethyl)-p-xylenes, respectively. Isomeric mixtures were also obtained. NMR data of the polyalkylated products prepared as above are listed in Table 8.

TABLE 8

$^1$H NMR data of poly(methyldichlorosilylethyl)-p-xylenes

| No. of subst. | NMR data (ppm) | | | | |
|---|---|---|---|---|---|
| (n) | Si—CH$_3$ | Si—CH$_2$ | Aryl—CH$_3$ | Aryl—CH$_2$ | Aryl—H |
| 3 | 0.79(s) | 1.34–1.46(m) | 2.31(s) | 2.80–2.85(m) | 7.02(s) |
| 4 | 0.88(s) | 1.28–1.34(m) | 2.29(s) | 2.80–2.85(m) | * |

Example 9

Reaction of Benzene With Vinyltrichlorosilane

In the same apparatus and by the same procedure as described in EXAMPLE 1, benzene 0.87 g (11.00 mmol), vinyltrichlorosilane 11.18 g (69.00 mmol) and aluminum chloride 0.3 g (2.25 mmol) were reacted at 80° C. for 1 hour under the dry nitrogen atmosphere. Recrystallization of solid product from THF gave 5.15 g (yield: 42.7%, bp: 135°–8° C.) of 1,2,4,5-tetrakis(trichlorosilylethyl)benzene. Distillation of the filtrate gave 0.73 g (yield: 6.04%, bp: 176°–9° C./0.6 mm), 7.41 g (yield: 61.5%, bp: 204°–10° C./0.6 mm) and 1.31 g (yield: 10.8%, bp: 261°–6° C./0.6 mm) of tris-, tetrakis- and pentakis(trichlorosilylethyl)benzenes, respectively isomeric mixtures were also obtained. NMR data of the polyalkylated products prepared as above are listed in Table 9.

TABLE 9

$^1$H NMR data of poly(trichlorosilylethyl)benzenes

| No. of Subst. | NMR data (ppm) | | |
|---|---|---|---|
| (n) | Si—CH$_2$ | Aryl-CH$_2$ | Aryl-H |
| 3 | 1.51–1.59 (m) | 2.81–2.98 (m) | 7.10–7.22 (m) |
| 4 | 1.61–1.69 (m) | 2.18–2.98 (m) | 7.02–7.14 (m) |
| 5 | 1.71–1.79 (m) | 2.81–2.98 (m) | 7.01 (s) |

Example 10 Reaction of Toluene With Vinyltrichlorosilane

In the same apparatus and by the same procedure as described in EXAMPLE 1, toluene 0.88 g (9.35 mmol), vinyltrichlorosilane 7.55 g (46.80 mmol) and aluminum chloride 0.12 g (0.90 mmol) were reacted at 80° C. for 6 hours under a dry nitrogen atmosphere. Recrystallization of solid product from THF gave 0.51 g (yield: 6.12%, bp: 264°–6° C.) of pentakis(trichlorosilylethyl)toluene. Distillation of the filtrate gave 3.37 g (yield: 40.1%, bp: 189°–92° C./0.6 mm) and 3.62 g (yield: 43.00%, bp: 224°–8° C./0.6 mm) of tris- and tetrakis(trichlorosilylethyl)toluenes, respectively. Isomeric mixtures were also obtained. NMR data of the polyalkylated products prepared as above are listed in Table 10.

Table 10. $^1$H NMR data of poly(trichlorosilylethyl) toluenes

| No. of subst. | NMR data (ppm) | | | |
|---|---|---|---|---|
| (n) | Si—CH$_2$ | Aryl-CH$_3$ | Aryl-CH$_2$ | Aryl-H |
| 3 | 1.62–1.72 (m) | 2.23–2.28 (m) | 2.78–2.88 (m) | 6.93–7.14 (m) |
| 4 | 1.62–1.72 (m) | 2.23–2.28 (m) | 2.78–2.88 (m) | 6.93 (s) |
| 5 | 1.52–1.59 (m) | 2.28 (s) | 2.78–2.88 (m) | * |

Example 11

Reaction of Ethylbenzene With Vinyltrichlorosilane

In the same apparatus and by the same procedure described in EXAMPLE 1, ethylbenzene 0.87 g (8.20 mmol), vinyltrichlorosilane 6.59 g (40.80 mmol) and aluminum chloride 0.47 g (3.52 mmol) were reacted at 80° C. for 6 hours under a dry nitrogen atmosphere. Recrystallization of solid product from THF gave 0.18 g (yield: 2.47%, mp: 195°–8° C.) of pentakis(trichlorosilylethyl) ethylbenzene. Distillation of the filtrate gave 1.56 g (yield: 18.6%, bp: 175°–9° C./0.6 mm), 1.20 g (yield: 14.3% bp: 221°–6° C./0.6 mm), 0.15 g (yield: 1.81%), 0.84 g (yield: 10.7%), 0.95 g (yield: 11.3%), 0.41 g (yield: 4.83%), 0.55 g (yield: 6.55%) and 0.66 g (yield: 7.86%) of tris-, tetrakis (trichlorosilylethyl)ethylbenzenes, bis-, tris-, tetrakis (trichlorosilylethyl)diethylbenzenes, tris-, tetrakis- and pentakis(trichlorosilylethyl)benzene respectively. Isomeric mixtures were also obtained. NMR data of the polyalkylated products prepared as above are listed in Table 11.

TABLE 11

$^1$H NMR data of poly(trichlorosilylethyl)ethylbenzenes

| No. of subst. | NMR data (ppm) | | | | |
|---|---|---|---|---|---|
| (n) | Et(CH$_3$) | Si—CH$_2$ | Et(CH$_2$) | Aryl—CH$_2$ | Aryl—H |
| 3 | 1.21–1.08(m) | 1.70–1.74(m) | 2.61–2.65(m) | 2.78–2.83(m) | 6.94–7.19(m) |
| 4 | 1.21–1.08(m) | 1.70–1.74(m) | 2.61–2.65(m) | 2.78–2.83(m) | 6.94–7.19(m) |
| 5 | 1.23(t) | 1.60–1.67(m) | 2.62(q) | 2.78–2.83(m) | * |

Example 12

Reaction of n-propylbenzene With Vinyltrichlorosilane

In the same apparatus and by the same procedure as described in EXAMPLE 1, n-propylbenzene 0.86 g (7.17 mmol), vinyltrichlorosilane 5.9 g (35.90 mmol) and aluminum chloride 0.047 g (0.35 mmol) were reacted at 80° C. for 6 hours under dry nitrogen atmosphere. Recrystallization of solid product from THF gave 0.18 g (yield: 2.86%, mp; 211°–6° C.) of pentakis(trichlorosilylethyl)-n-propylbenzene. Distillation of the filtrate gave 2.43 g (yield: 36.51%, bp: 192°–8° C./0.6 mm), 2.00 g (yield: 30.0%, bp: 220°–5° C./0.6 mm), 0.61 g (yield: 9.15%), 0.14 g (yield: 2.05%) and 0.24 g (yield: 3.59%) of tris-, tetrakis (trichlorosilylethyl)-n-propylbenzenes, tetrakis (trichlorosilylethyl)dipropylbenzene, mono- and bis (trichlorosilylethyl)benzenes, respectively. Isomeric mixtures were also obtained. NMR data of the polyalkylated products prepared as above are listed in Table 12.

TABLE 12

$^1$H NMR data of poly(trichlorosilylethyl)-n-propylbenzenes

| No. of Subst | NMR data (ppm) | | | | | |
|---|---|---|---|---|---|---|
| (n) | Pr(CH$_3$) | SI—CH$_2$ | Pr(CH$_2$) | Pr(CH$_2$) | Aryl—CH$_2$ | Aryl—H |
| 3 | 1.02–1.08(m) | 1.70–1.74(m) | 1.74–1.79(m) | 2.53–2.55(m) | 2.78–2.83(m) | 6.94–7.19(m) |
| 4 | 1.02–1.08(m) | 1.70–1.74(m) | 1.74–1.79(m) | 2.53–2.55(m) | 2.78–2.83(m) | 6.94–7.19(m) |
| 5 | 1.04(t) | 1.60–1.67(m) | 1.74–1.79(m) | 2.54(t) | 2.78–2.83(m) | |

Example 13

Reaction of n-butylbenzene With Vinyltrichlorosilane

In the same apparatus and by the same procedure described in EXAMPLE 1, n-butylbenzene 0.86 g (6.40 mmol), vinyltrichlorosilane 5.17 g (32.00 mmol) and aluminum chloride 0.047 g (0.35 mmol) were reacted at 80° C. for 6 hours under a dry nitrogen atmosphere. Recrystallization of solid product from THF gave 6.16 g (yield: 2.68%, mp: 228°–35° C.) of pentakis(trichlorosilylethyl)-n-butylbenzene. Distillation of the filtrate gave 2.20 g (yield:

36.59%, bp: 192°–8° C./0.6 mm), 1.81 g (yield: 30.0%, bp: 220°–5° C./0–6 mm), 0.63 g (yield: 10.15%), 0.12 g (yield: 2.05%) and 0.22 g (yield: 3.59%) of tris-, tetrakis (trichlorosilylethyl)-n-butylbenzenes, tetrakis (trichlorosilylethyl)dibutylbenzene, mono- and bis (trichlorosilylethyl)benzenes, respectively. isomeric mixtures were also obtained. NMR data of the polyalkylated products prepared as above are listed in Table 13.

TABLE 13

1H NMR data of poly(trichlorosilylethyl)-n-butylbenzenes

| No. of Subst (n) | NMR data (ppm) | | | | |
|---|---|---|---|---|---|
| | Bu(CH$_3$) | Si—CH$_2$ | Bu(CH$_2$CH$_2$) | Bu(CH$_2$) | Aryl—CH$_2$ | Aryl—H |
| 3 | 1.02–1.08(m) | 1.72–1.76(m) | 1.74–1.79(m) | 2.54–2.56(m) | 2.78–2.83(m) | 6.94–7.19(m) |
| 4 | 1.02–1.08(m) | 1.72–1.76(m) | 1.74–1.79(m) | 2.53–2.56(m) | 2.78–2.83(m) | 6.94–7.19(m) |
| 5 | 1.04(t) | 1.62–1.69(m) | 1.74–1.79(m) | 2.55(t) | 2.78–2.83(m) | * |

Example 14

Reaction of o-xylene With Vinyltrichlorosilane

In the same apparatus and by the same procedure as described in EXAMPLE 1, o-xylene 0.87 g (8.21 mmol), vinyltrichlorosilane 5.27 g (32.80 mmol) and aluminum chloride 0.096 g (0.72 mmol) were reacted at 80° C. for 2 hours under a dry nitrogen atmosphere. Recrystallization of solid product from THF gave 0.83 g (yield: 15.1%) of tetrakis(trichlorosilylethyl)-p-xylene. Distillation of the filtrate gave 1.99 g (yield: 32.9%, bp: 193°–8° C./0.6 mm) and 1.91 g (yield: 30.3%, bp: 240°–2° C./0.6 mm) of tris- and tetrakis(trichlorosilylethyl)-o-xylenes, respectively. Isomeric mixtures were also obtained. NMR data of the polyalkylated products prepared as above are listed in Table 14.

TABLE 14

$^1$H NMR data of poly(trichlorosilylethyl)-o-xylenes

| No. of subst. (n) | NMR data (ppm) | | | |
|---|---|---|---|---|
| | Si—CH$_2$ | Aryl-CH$_3$ | Aryl-CH$_2$ | Aryl-H |
| 3 | 1.63–1.72 (m) | 2.24–2.28 (m) | 2.84–2.90 (m) | 6.89–6.93(m) |
| 4 | 1.52–1.59 (m) | 2.30 (s) | 2.84–2.90 (m) | * |

Example 15

Reaction of m-xylene With Vinyltrichlorosilane

In the same apparatus and by the same procedure as described in EXAMPLE 1, m-xylene 0.87 g (8.20 mmol), vinyltrichlorosilane 5.27 g (32.80 mol) and aluminum chloride 0.14 g (0.82 mmol) were reacted at 80° C. for 2 hour under a dry nitrogen atmosphere. Recrystallization of solid product from THF gave 2.46 g (yield: 40.0%) of tetrakis (trichlorosilylethyl)-p-xylene. Distillation of the filtrate gave 2.28 g (yield: 37.1%, bp: 192°–8° C./0.6 mm) and 0.49 g (yield: 8.05%, bp: 241°–5° C./0.6 mm) of tris- and tetrakis (trichlorosilylethyl)-m-xylenes, respectively. Isomeric mixtures were also obtained. NMR data of the polyalkylated products prepared as above as listed in Table 15.

TABLE 15

$^1$H NMR data of poly(trichlorosilylethyl)-m-xylenes

| No. of subst. (n) | NMR data (ppm) | | | |
|---|---|---|---|---|
| | Si—CH$_2$ | Aryl-CH$_3$ | Aryl-CH$_2$ | Aryl-H |
| 3 | 1.63–1.72 (m) | 2.24–2.28 (m) | 2.84–2.90 (m) | 6.89–6.93 (m) |
| 4 | 1.52–1.59 (m) | 2.30 (s) | 2.84–2.90 (m) | * |

Example 16

Reaction of p-xylene With Vinyltrichlorosilane

In the same apparatus and by the same procedure as described in EXAMPLE 1, p-xylene 0.87 g (8.19 mmol), vinyltrichlorosilane 5.27 g (32.8 mmol) and aluminum chloride 0.11 g (0.82 mmol) were reacted at 80° C. for 2 hours under a dry nitrogen atmosphere. Recrystallization of solid product from THF gave 2.74 g (yield: 45.4%, mp; 220°–4° C.) of tetrakis(trichlorosilylethyl)-p-xylene. Distillation of the filtrate gave 1.99 g (yield: 32.9%, bp; 192°–8° C./0.6 mm) of tris (trichlorosilyethyl)-p-xylene. An isomeric mixture was also obtained. NMR data of the polyalkylated products prepared as above are listed in Table 16.

TABLE 16

$^1$H NMR data of poly(trichlorosilylethyl)-p-xylenes

| No. of subst. (n) | NMR data (ppm) | | | |
|---|---|---|---|---|
| | Si—CH$_2$ | Aryl-CH$_3$ | Aryl-CH$_2$ | Aryl-H |
| 3 | 1.63–1.72 (m) | 2.24–2.28 (m) | 2.84–2.90 (m) | 6.89–6.93(m) |
| 4 | 1.52–1.59 (m) | 2.30 (s) | 2.84–2.90 (m) | * |

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A compound containing chlorosilyl groups represented by formula III

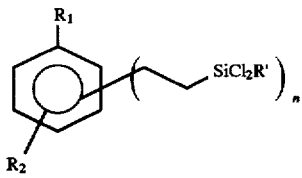

Formula III wherein $R_1$ represents hydrogen or alkyl; $R_2$ represents hydrogen or alkyl; R' represents methyl or chloro; and n=3–6.

2. The compound of claim 1, wherein $R_1$ is $C_{1-10}$-alkyl.
3. The compound of claim 2, wherein $R_1$ is $C_{1-4}$-alkyl.
4. The compound of claim 1, wherein $R_2$ is $C_{1-10}$-alkyl.
5. The compound of claim 4, wherein $R_2$ is methyl.
6. The compound of claim 1, wherein n=3.
7. The compound of claim 1, wherein n=4.
8. The compound of claim 1, wherein n=5.
9. The compound of claim 1, wherein n=6.
10. A method of preparing a compound of formula III,

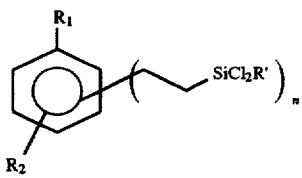

Formula III wherein $R_1$ is hydrogen or alkyl; $R_2$ is hydrogen or alkyl; R' is methyl or chloro and n=3–6, comprising:

reacting a benzene compound of formula I with a vinylchlorosilane of formula II in the presence of a Lewis acid catalyst

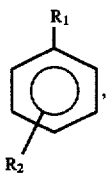

Formula I

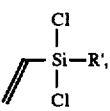

Formula II wherein $R_1$, $R_2$, and R' and n are as defined above.

11. The method of claim 10, wherein said catalyst is aluminum chloride.

12. The method of claim 11, wherein the amount of vinylchlorosilane ranges from 0.01–20 moles per mole of said benzene compound.

13. The compound of claim 1, wherein $R_1$ and $R_2$ are each alkyl.

14. The compound of claim 13, wherein $R_1$ and $R_2$ are each $C_{1-10}$-alkyl.

15. The compound of claim 13, wherein $R_1$ and $R_2$ are each $C_{1-4}$-alkyl.

16. The compound of claim 13, wherein $R_1$ and $R_2$ are each methyl.

17. The method of claim 10, wherein $R_1$ and $R_2$ are each alkyl.

18. The method of claim 17, wherein $R_1$ and $R_2$ are each $C_{1-10}$alkyl.

19. The method of claim 17, wherein $R_1$ and $R_2$ are each $C_{1-4}$-alkyl.

20. The method of claim 17, wherein $R_1$ and $R_2$ are each methyl.

* * * * *